(12) United States Patent
Deshpande (10) Patent No.: US 8,991,396 B2
(45) Date of Patent: Mar. 31, 2015

(54) ENDOTRACHEAL TUBE WITH TWO PORTS

(75) Inventor: Girish G. Deshpande, Peoria, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1207 days.

(21) Appl. No.: 11/937,195

(22) Filed: Nov. 8, 2007

(65) Prior Publication Data

US 2008/0110467 A1    May 15, 2008

Related U.S. Application Data (60) Provisional application No. 60/858,034, filed on Nov. 9, 2006.

(51) Int. Cl.
| | | |
|---|---|---|
| A62B 9/06 | (2006.01) | |
| A61M 16/00 | (2006.01) | |
| A61M 16/04 | (2006.01) | |

(52) U.S. Cl.
CPC ....... *A61M 16/0463* (2013.01); *A61M 16/0434* (2013.01); *A61M 2016/0413* (2013.01); *A61M 16/0427* (2014.02); *A61M 16/0493* (2014.02); *A61M 2205/32* (2013.01)
USPC .................................................. 128/207.14

(58) Field of Classification Search
USPC ........... 128/207.14, 207.15, 207.17; 604/284, 604/533–537; 285/148.4, 125.1–127.2, 285/132.1–133.21, 272, 282, 121.6, 121.3, 285/121.5
See application file for complete search history.

(56) References Cited

U.S. PATENT DOCUMENTS

| | | | | |
|---|---|---|---|---|
| 1,128,634 | A * | 2/1915 | Talbot | 285/91 |
| 2,684,860 | A * | 7/1954 | Rafferty | 285/85 |
| 3,667,475 | A * | 6/1972 | Venturelli et al. | 128/207.14 |
| 4,152,017 | A | 5/1979 | Abramson | |
| 4,416,273 | A * | 11/1983 | Grimes | 128/207.16 |
| 4,595,005 | A * | 6/1986 | Jinotti | 128/205.24 |
| 4,815,459 | A * | 3/1989 | Beran | 128/207.14 |
| 5,226,426 | A * | 7/1993 | Yoon | 600/566 |
| 5,279,549 | A * | 1/1994 | Ranford | 604/34 |
| 5,507,284 | A * | 4/1996 | Daneshvar | 128/207.14 |
| 5,546,936 | A * | 8/1996 | Virag et al. | 128/207.14 |
| 5,558,376 | A * | 9/1996 | Woehl | 285/91 |
| 5,694,922 | A * | 12/1997 | Palmer | 128/202.27 |
| 5,964,223 | A * | 10/1999 | Baran | 128/207.14 |
| 6,394,092 | B1 * | 5/2002 | Barrett et al. | 128/207.17 |
| 6,615,835 | B1 * | 9/2003 | Cise et al. | 128/207.14 |
| 6,892,729 | B2 * | 5/2005 | Smith et al. | 128/204.18 |

(Continued)

OTHER PUBLICATIONS

Tindol GA, DiBenedetto RJ, Kosciuk L. Unplanned extubations. Chest, 105:1804-1807, 1994.

(Continued)

*Primary Examiner* — Justine Yu
*Assistant Examiner* — Michael Tsai
(74) *Attorney, Agent, or Firm* — McDonnell Boehnen Hulbert & Berghoff LLP (57) ABSTRACT

An endotracheal tube apparatus with two ports. The first port extends from a patient's mouth in a direction substantially in line with the patients oral cavity. The second port extends from a patient's mouth in a second direction. An endotracheal tube adapted to be inserted in a patient's trachea through the patient's mouth, is in fluid communication with the first port and the second port. The second port of the endotracheal tube apparatus may be adapted to be secured to a patient's mandible. The endotracheal tube apparatus may have at least two locations for securing the apparatus to a patient.

23 Claims, 10 Drawing Sheets

(56) References Cited

U.S. PATENT DOCUMENTS

| | | | | |
|---|---|---|---|---|
| 6,895,966 | B2* | 5/2005 | Christopher | 128/207.15 |
| 7,478,636 | B2* | 1/2009 | Madsen et al. | 128/207.15 |
| 7,581,541 | B2* | 9/2009 | Madsen et al. | 128/207.14 |
| 2004/0181192 | A1* | 9/2004 | Cuppy | 604/256 |
| 2006/0005841 | A1* | 1/2006 | Anderson et al. | 128/207.14 |
| 2010/0242957 | A1* | 9/2010 | Fortuna | 128/202.22 |

OTHER PUBLICATIONS

Boulain T et al. Unplanned extubations in the Adult Intensive Care Unit—A prospective multi-center study. Am J Respir Crit Care Med, 157: 1131-1137, 1998.

Vassal T, Anh NGD, Guidet JM, et al. Prospective evaluation of Inadvertentextubations in a medical intensive care unit. Intensive Care Med, 19: 340-342, 1993.

Marcin JP, Rutan E, Tapetti PM et al. Nurse Staffing and unplanned extubation in the pediatric intensive care units. Pediatr Crit Care Med, 6: 254-257, 2005.

Lassence Ad, Alberti C, Azoulay E et al. Impact of unplanned extubations and reintubation after weaning on Nosocomial pneumonia risk in the Intensive Care Unit: A prospectiv.

Torres A, Gatell JM, Aznar E, et al. Re-intubation Increases the Risk of Nosocomial Pneumonia in Patients Needing Mechanical Ventilation. Am J Respir Crit Care Med, 152: 137.

Scott PH, Eigen H, Moye LA, et al. Predictability and Consequences of Spontaneous extubation in a pediatric ICU. Crit Care Med, 13: 228-232, 1985.

Nakagishi Y, Morimoto Y. Fujita M, et al. Rabbit Model of Airway Stenosis Induced by Scraping of the Tracheal Mucosa. Laryngoscope, 115: 1087-1092, 2005.

Orlowski JP, Ellis NG, Amin NP et al. Complications of airway intrusion in 100 consecutive cases in a pediatric ICU. Crit Care Med, 8: 324-331, 1980.

* cited by examiner

Measurements and sizes:

| Number | Internal Diameter | Distance from Distal end to curved port 'B' | Total length of tube 'A' |
|---|---|---|---|
| 3.0 | 3 mm | 9 cm | 12 cm |
| 3.5 | 3.5 mm | 10.5 cm | 13.5 cm |
| 4.0 | 4 mm | 12 cm | 15 cm |
| 4.5 | 4.5 mm | 13.5 cm | 16.5 cm |
| 5.0 | 5 mm | 15 cm | 18 cm |
| 5.5 | 5.5 mm | 16.5 cm | 19.5 cm |
| 6.0 | 6 mm | 18 cm | 21 cm |
| 6.5 | 6.5 mm | 19.5 cm | 22.5 cm |
| 7.0 | 7 mm | 21 cm | 24 cm |
| 7.5 | 7.5 mm | 22.5 cm | 25.5 cm |

FIGURE 10

ENDOTRACHEAL TUBE WITH TWO PORTS

CROSS-REFERENCE TO RELATED APPLICATIONS

This application claims priority from U.S. Provisional Patent Application No. 60/858,034 filed Nov. 9, 2006.

STATEMENT REGARDING FEDERALLY SPONSORED RESEARCH

Not Applicable.

APPENDIX

Not Applicable.

BACKGROUND OF THE INVENTION

1. Field of the Invention

The present invention is a new design having several advantages over the currently used endotracheal tubes.

2. Related Art

Patients requiring respiratory support in the form of mechanical ventilation often need an access to the airway in the form of endotracheal tube or tracheostomy tube. Endotracheal tube placement is also called intubation. In addition to providing an entry to the airway for mechanical ventilation it also serves as a port for clearing of respiratory secretions, delivering aerosolized medications such as albuterol, and other medical gases such as anesthetics, nitric oxide, helium. Presence of endotracheal tube also makes it easier to perform Fiberoptic bronchoscopy.

Once placed it is important that endotracheal tube stays inside the trachea until the duration that it is needed for. Inadvertent extubation is a frequent and serious complication of mechanical ventilation. The incidence of inadvertent extubation varies from 3% to 16% in adult population (1, 2, 3) and 2.7 to 5.5% in pediatric patients (4). Inadvertent extubation is associated with significant complications such as increased duration of mechanical ventilatory support, increased duration of hospital stay, and also increased incidence of nosocomial pneumonia (5,6).

There are several retrospective and some prospective studies showing that patient's age, severity of illness, the use of patient restraints, the method of sedation delivery, years of ICU nurse experience, and repositioning have no effect on the incidence of unplanned extubation (7).

Currently used endotracheal tubes are made up of PVC plastic, having a uniform curve and have a single distal port. Oral endotracheal tubes are secured at only one position on the tube with tape or other device to a patient's lip. The distal opening of the ET tube is fitted with an adapter which in turn is connected to ventilator tubings, in-line suction tubing, etc. An end-tidal carbon dioxide monitor and tidal volume monitor are sometimes interposed between the endotracheal tube adapter and ventilator tubing for closer monitoring. This contraption at the end of the endotracheal tube adds additional weight, keeping a constant pull on the ET tube in outward direction making it vulnerable for inadvertent extubation. This when added with some efforts from the patient or movement of the patient during transport or nursing care could result in inadvertent extubation.

Movement of patient's head and neck could result in movement of the ET tube in and out of patient's mouth when the tape comes loose, as for example from oral secretions. This movement of the tube can damage the inside of trachea by scraping the mucosa, making it prone to develop inflammatory edema initially and scarring and narrowing later, as shown in an animal model by Nakagishi et al (8).

Naso-tracheal intubation is an alternative option for accessing the airway. Nasal tubes are more easily anchored, have less extraneous movement, permit closure of mouth and are better tolerated by most patients. However, nasal tubes are associated with slightly higher morbidity than orotracheal tubes; these are longer, occasionally narrower and more prone for obstruction from secretions and kinking (9). They also offer a greater resistance to airflow.

The former endotracheal tubes are secured only at one area on the tube with a tape/device that is then secured at the lip or the nose. This process makes the endotracheal tubes vulnerable for inadvertent extubation and/or kinking especially with the weight of the attached tubings and paraphernalia that goes with it (such as in-line suction, CO2 sensors, etc.). The tape or securing device acts as fulcrum with a short arm as ventilator tubings with weights (in-line suction, end-tidal CO2 meter etc.) and a long arm as endotracheal tube, thus even a small movement at the short arm translates to a bigger movement of the long arm (endotracheal tube) resulting in inadvertent extubation.

The common features of current endotracheal tubes are: they are used to provide direct and unobstructed airway; they are made from special non-toxic, clear, thermo-sensitive siliconised PVC material to protect delicate mucosa; all tubes are fitted with 15-mm standard connector, which insures compatibility with circuit connectors; they provide full-length radio-opaque line to assess exact location of tube; they have 1-cm graduation markings to ascertain insertion depth; they are latex free; they are available in different sizes.

The main disadvantage of the current endotracheal tube is that it is liable for inadvertent extubation because:

a. It is difficult to secure b. The weight of the tubings, and other paraphernalia makes ET tube unstable and precarious and prone to extubation and kinking.

c. Side to side movement of the head not only results in inadvertent extubation but also can be damaging to subglottic area and inner lining of the trachea.

REFERENCES

1. Tindol G A, DiBenedetto R J, Kosciuk L. Unplanned extubations. Chest, 105:1804-1807, 1994.
2. Boulain T et al. Unplanned extubations in the Adult Intensive Care Unit—A prospective multi-center study. Am J Respir Crit Care Med, 157: 1131-1137, 1998.
3. Vassal T, Anh N G D, Guidet J M, et al. Prospective evaluation of Inadvertent extubations in a medical intensive care unit. Intensive Care Med, 19: 340-342, 1993.
4. Marcin J P, Rutan E, Tapetti P M et al. Nurse Staffing and unplanned extubation in the pediatric intensive care units. Pediatr Crit Care Med, 6: 254-257, 2005.
5. Lassence Ad, Alberti C, Azoulay E et al. Impact of unplanned extubations and reintubation after weaning on Nosocomial pneumonia risk in the Intensive Care Unit: A prospective multi-center study. Anesthesiology, 97: 148-156, 2002.
6. Torres A, Gatell J M, Aznar E, et al. Re-intubation Increases the Risk of Nosocomial Pneumonia in Patients Needing Mechanical Ventilation. Am J Respir Crit Care Med, 152: 137-141, 1995.
7. Scott P H, Eigen H, Moye L A, et al. Predictability and Consequences of Spontaneous extubation in a pediatric ICU. Crit Care Med, 13: 228-232, 1985.

8. Nakagishi Y, Morimoto Y. Fujita M, et al. Rabbit Model of Airway Stenosis Induced by Scraping of the Tracheal Mucosa. Laryngoscope, 115: 1087-1092, 2005.
9. Orlowski J P, Ellis N G, Amin N P et al. Complications of airway intrusion in 100 consecutive cases in a pediatric ICU. Crit Care Med, 8: 324-331, 1980.

SUMMARY OF THE INVENTION

The new endotracheal tube has two ports: 1. A straight port (short) used for stylet (used during intubation procedure), suction tubing, and introduction of other apparatuses such as a bronchoscope or in-line suction or endotracheal tube exchanger devices; and 2. A distal (curved) port used for connecting endotracheal tube to the ventilator and sensors such as used for end-tidal carbon dioxide measurement.

The new endotracheal tube may have all the common features stated above for the current endotracheal tubes with an exception of the ventilator end of the tube being different.

The new tube will be secured not only at the lip but also along the mandible, thus minimizing the chance of inadvertent extubation.

The new tube design also distributes the weight of the other accessories on ports, thus again minimizing the chance of inadvertent extubation.

As the new tube is also secured along the mandible, the whole tube will move with side to side movements of the head, which used to be a problem with the old straight tubes. This reduces the trauma that can happen to vocal cords or subglottic region from side to side movement of the head.

As the straight port is closer to the lip and is shorter, the new tube facilitates the introduction of a bronchoscope or other devices.

As the new tube is secured at two areas on the tube, there is less chance of inadvertent extubation of the tube, for example, while re-taping the tube.

The new tube has a locking rotation mechanism to move a mandibular anchor site over from one side of the face to the other side thus minimizing skin trauma caused by long term attachment to only one side of the face.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

The new endotracheal tube 10, 110, 210 has two ports.

A straight port (short) 12, 112, 212 is used for; a stylet (a stiff wire used during intubation procedure), suction tubing/in-line suction, or introduction of other apparatus such as a bronchoscope or endotracheal tube exchanger device. The straight port is closer to the lip and is short, advantageously facilitating the introduction of a bronchoscope or other devices. A curved port (distal/long) 14, 114, 214 used for; connecting patient's airway to ventilator tubings, and to attach sensors such as end-tidal $CO_2$/tidal volume measuring devices.

The new tube is secured at two places thus making it less liable for displacement. It is first secured at the lip 22, as prior art devices were. It is next secured at the mandible 24.

The new tube is secured to the mandible, thus the whole tube moves with side-to-side movement of the head thus minimizing accidental extubation or damage to vocal cords and subglottic region.

As the new tube is secured at two places, there is less chance of inadvertent falling out of the tube while re-taping the tube. The new tube distributes the weight of accessories. The new tube may have a mechanism (rotator cuff) 130, 230 to move a mandibular anchor portion over from one side of the face to the other, thus minimizing skin trauma caused by long term attachment to only one side of the face.

FIGS. 3 through 7 depict a first embodiment. The split and rotating endotracheal tube 110 of the present invention includes a straight port 112 and a curved port 114. Curved port 114 is shaped and dimensioned to include a mandibular portion 116 which, when the tube is in place in the patient, lies adjacent to and/or in contact with the patient's mandible. Thus, the mandibular portion 116 provides a second anchoring position for the endotracheal tube by such standard means as taping. The novel structure of the endotracheal tube 110 allows this second anchoring without diverting, bending or kinking either line 112 or 114. The second anchoring position advantageously contributes to the prevention of inadvertent extubations. Mandibular portion 116 may be anchored to either side of the patient's mandible.

The endotracheal tube is further comprised of cuff 120, manifold 122 and locking ring 124. The cuff 120 includes a cylindrical seat 126 dimensioned to receive in close cooperation tube 128 which is the endotracheal tube portion that is installed in a patient's mouth, throat and trachea. The cuff 120 is further comprised of an annular ring 130 having integrally formed proximal and distal steps 132 and 134.

The manifold 122 is further comprised of a seat 136 for the straight port 112. Seat 136 is generally cylindrical and dimensioned to receive in close cooperation straight port tube 138. Manifold 122 is further comprised of ferrule 140 which includes an integrally formed seat 142 dimensioned to receive in close cooperation ventilator curved port tube 144, which will typically be used for ventilation. Within manifold 122 are a straight port lumen 146 and a ferrule lumen 148. Cuff 120 also includes an exit lumen 150. The internal diameter of endotracheal tube 128, cuff exit lumen 150, straight port internal lumen 146, ferrule lumen 148, straight port tube 138 and ferrule tube 144 are all constructed and dimensioned to avoid any flow restrictions. That is to say, the internal diameter of all these components is substantially equivalent in the depicted embodiment. This dimension may be 2.5 millimeters or 8.5 millimeters, such as are consistent with commonly used endotracheal tube components and ventilators, or may be other dimensions and remain within the scope of the present invention. Of note is the juncture 152 of the ferrule lumen 148 and straight port lumen 146 which also is constructed and dimensioned to avoid flow restrictions. In the depicted embodiments, the second port is located at a point on the endotracheal tube that is equivalent to or within ½ cm. of a distance that is 30 times the tube's diameter from the distal end of the endotracheal tube, for pediatric patients. For adults, the ratio to determine the point is the same, but the fork is within 1 cm of the point. See, FIG. 10.

Manifold 142 has a proximal end including a groove 154 which is defined between two annular rings 156 and 158. Groove 154 is dimensioned to receive a corresponding inward facing annular ring 160 in the lock ring 124. A leading or proximal face of inner, proximal manifold ring 158 is inclined such that the manifold 122 may be assembled with the locking ring 124 in a snap fit. The more distal or outer manifold ring 156 has a larger diameter than the inner proximal ring 158 in order to maintain locking ring 124 in its proper assembled position. Finally, the manifold's proximal section includes an annular extension 164 which after assembly abuts the distal step 134 of the annular ring 130 and cuff 120.

As is clear to those of skill in the art, the above described interaction interassembly of cuff 120, locking ring 124 and manifold 122 allows for the manifold 122, and accordingly ferrule 140 and ventilator tube 144 to be rotated around cuff 120 and endotracheal tube 128. It will also be apparent to those of skill in the art that the rotation of the manifold 122 may be achieved without rotation of cuff 120 and the endotracheal tube 128. This leaves the endotracheal tube 128, which is curved, unmoved within the patient's airway when the device is rotated. This is advantageous because over time the endotracheal tube 128 may become stiff. Stiff, curved tubes, if rotated within the patient, can damage the internal mucosal surfaces of the patient's airway.

Figure 7:
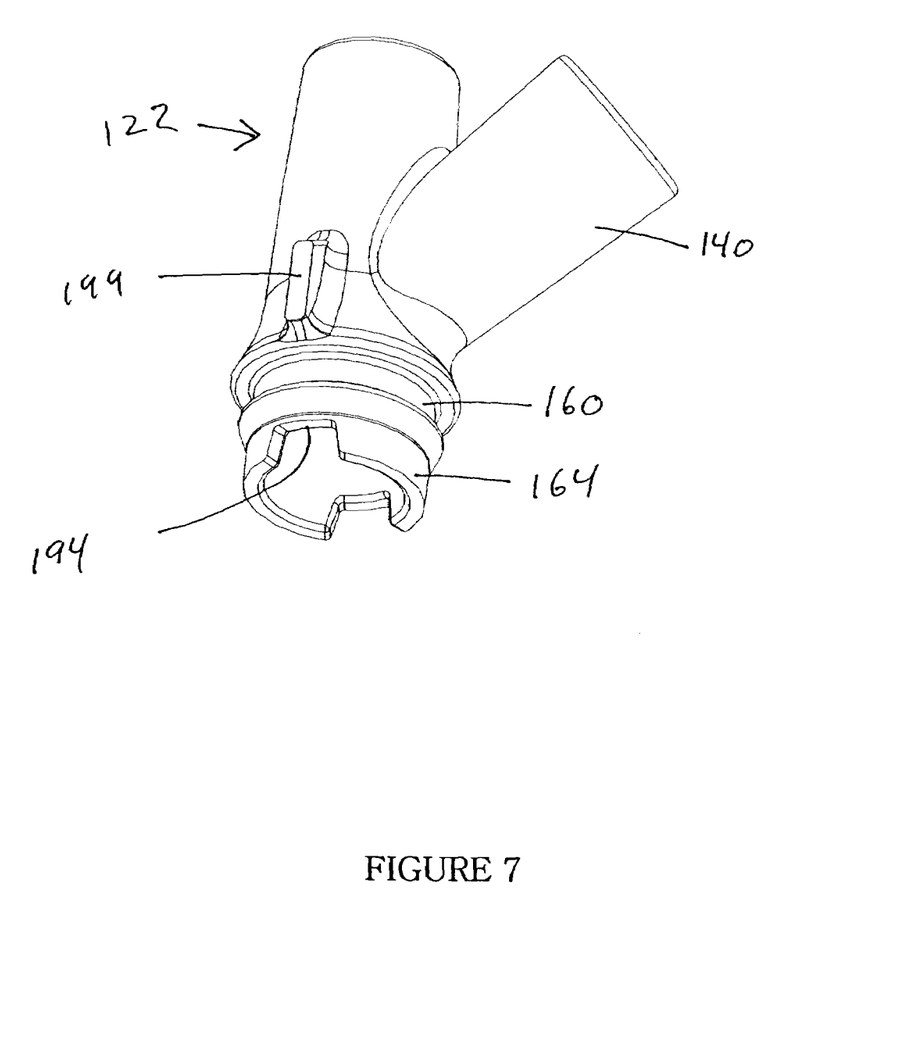
FIG. 7 is a disassembled view.

The position of ferrule 140 and ventilator 144 may be advantageously limited to either of two positions. These positions correspond to the left and right side of the patient's mandible, which are the optimal positions for anchoring the mandibular portion 116 of the ventilator tube 144. Accordingly, a novel interaction of manifold extension 164, the annular ring 130 of cuff 120 and locking ring 124 provides for locking the device at either position, and moreover for unlocking the device for rotation between the two positions. As is best seen in FIG. 7, manifold extension 164 includes, in the depicted embodiment, two notches 194 each having a shorter axial dimension than the remainder of the manifold extension 164. The annular ring 130 of cuff 120 has two corresponding bosses or teeth 184 having a greater annular dimension than the remainder of ring 130. The cuff tooth 184 corresponds to the manifold extension notch 194. Accordingly, to rotate the device, the locking ring 124 is moved axially outward away from the patient (upward in FIG. 4) through dimension 170, which corresponds to the axial dimension of notches 194 and teeth 184. Thus, when axially slid outwardly, the teeth 184 are removed from their seat in notches 194, thus allowing the rotation of one relative to the other. The user then rotates the device so that the ventilator tube 114 is proximate to the other side of the patient's mandible. The user then slides the locking ring 124 approximately again, reengaging teeth 184 with notches 194 and the device is again locked in its second alternate position. The seating of teeth 184 and notches 194 prevents the rotation of the device out of either of the two positions.

Figure 1:
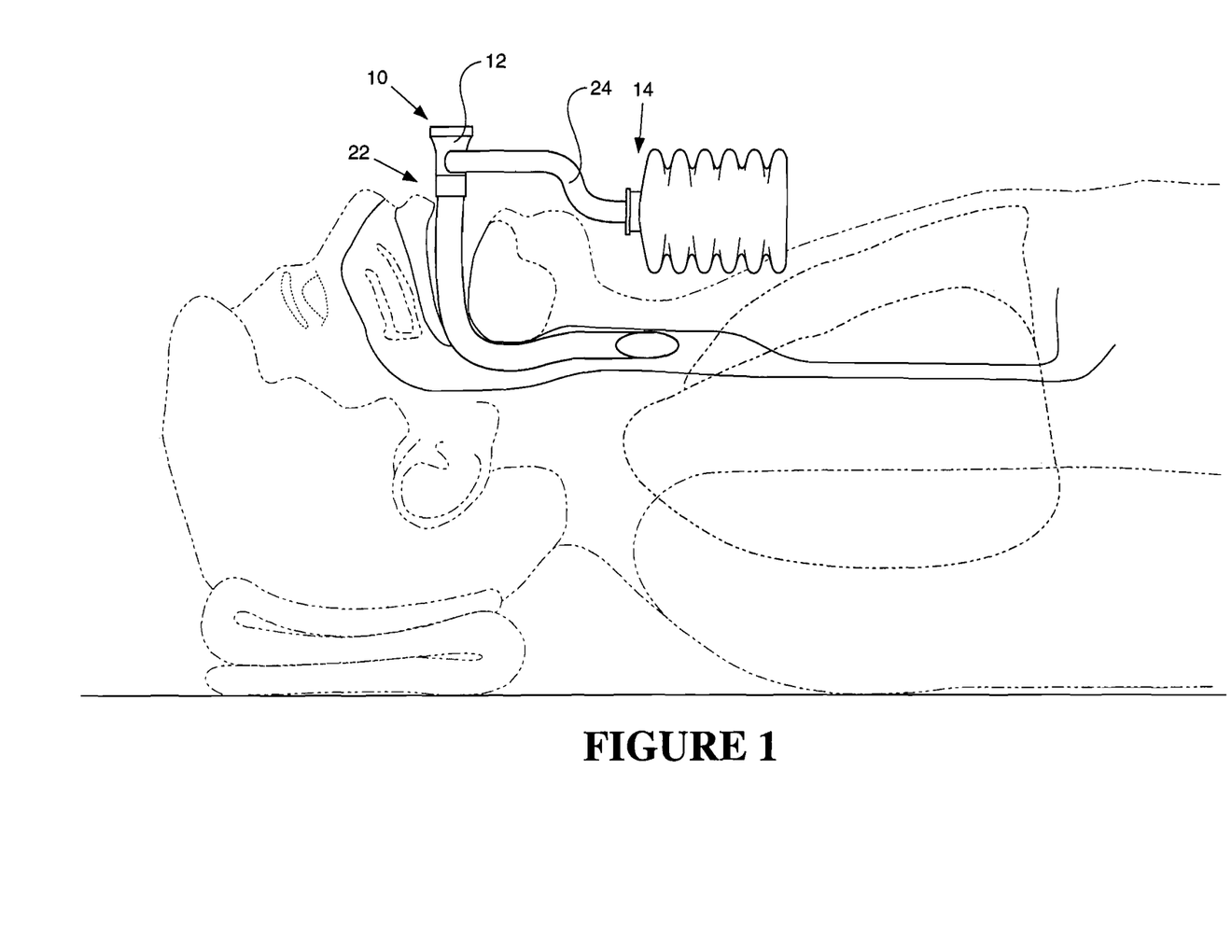
FIG. 1 is a side view of the endotracheal tube in position.
Figure 2:
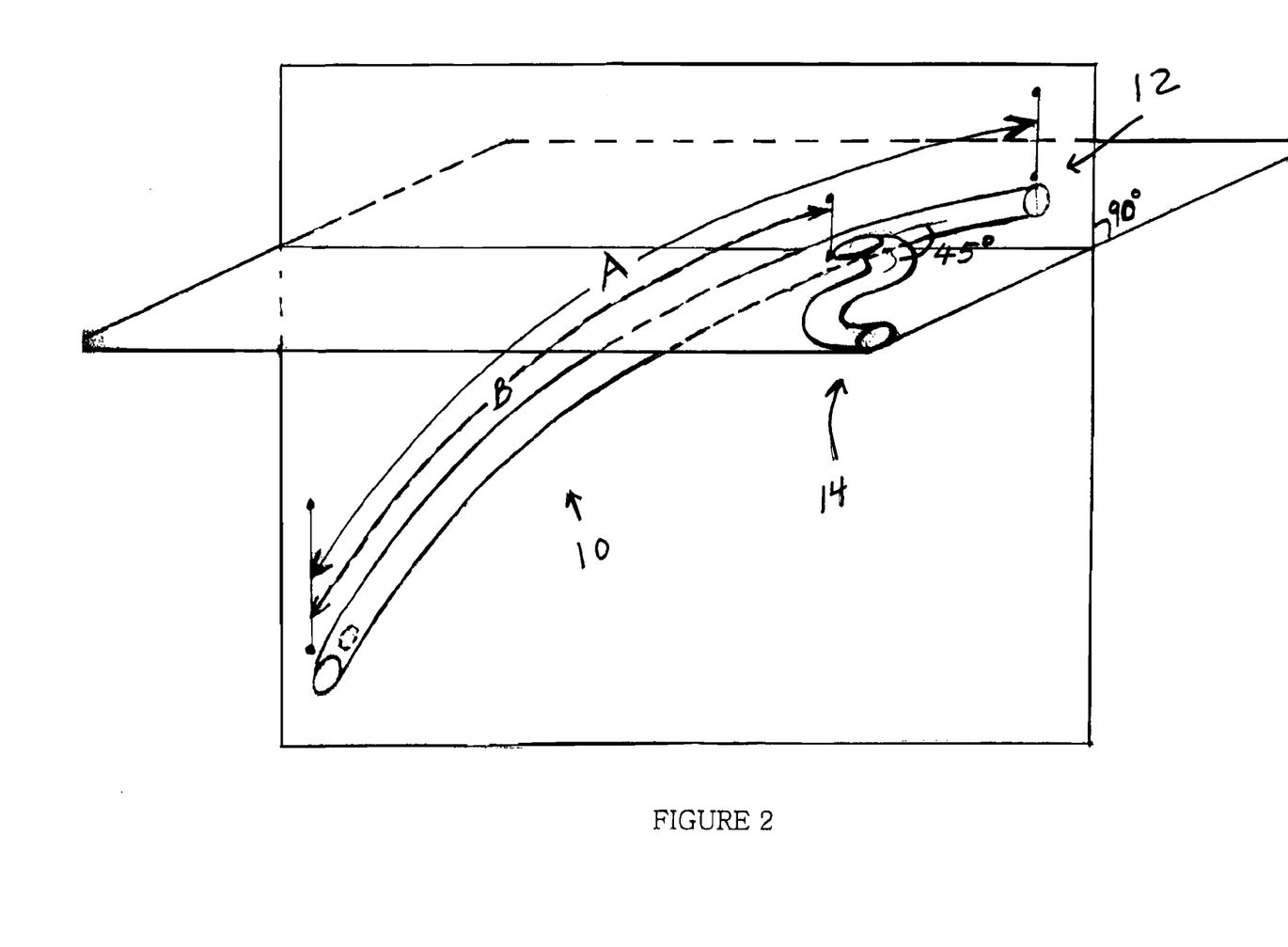
FIG. 2 is a schematic side view showing coordinates.
Figure 3:
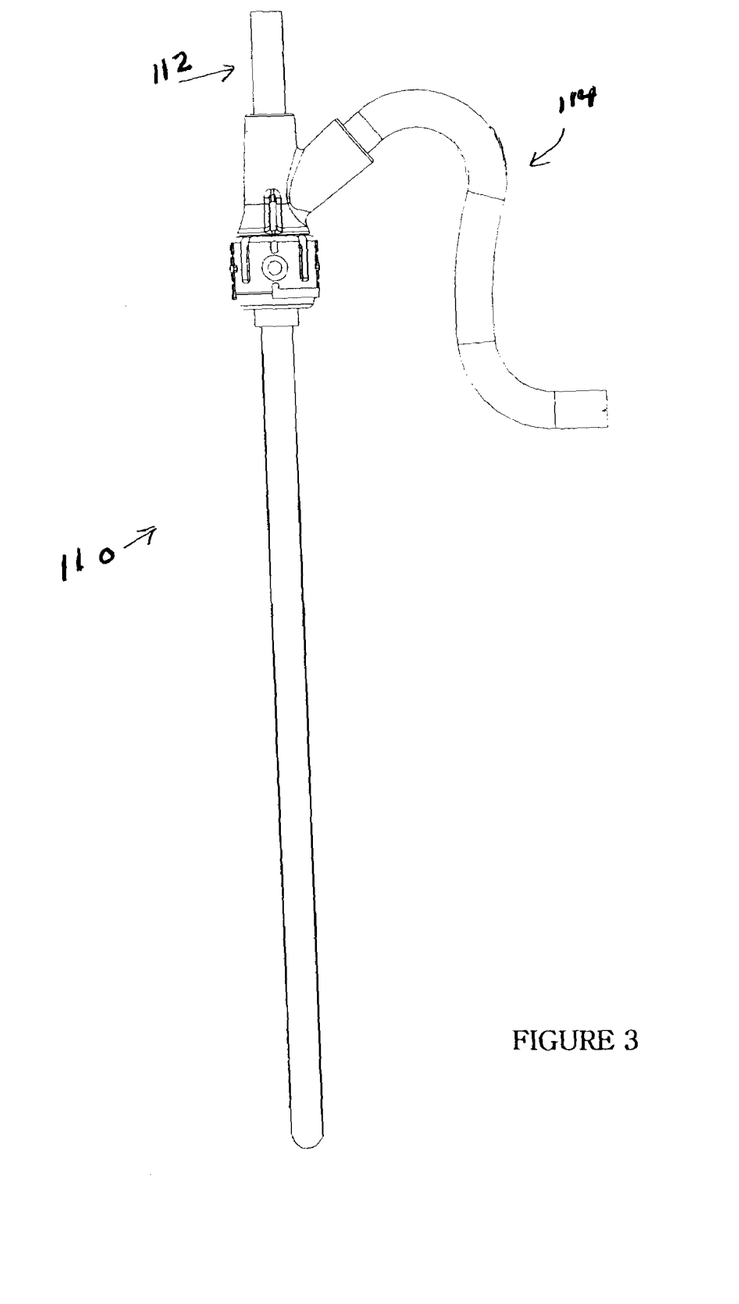
FIG. 3 is a frontal view of a first embodiment.
Figure 4:
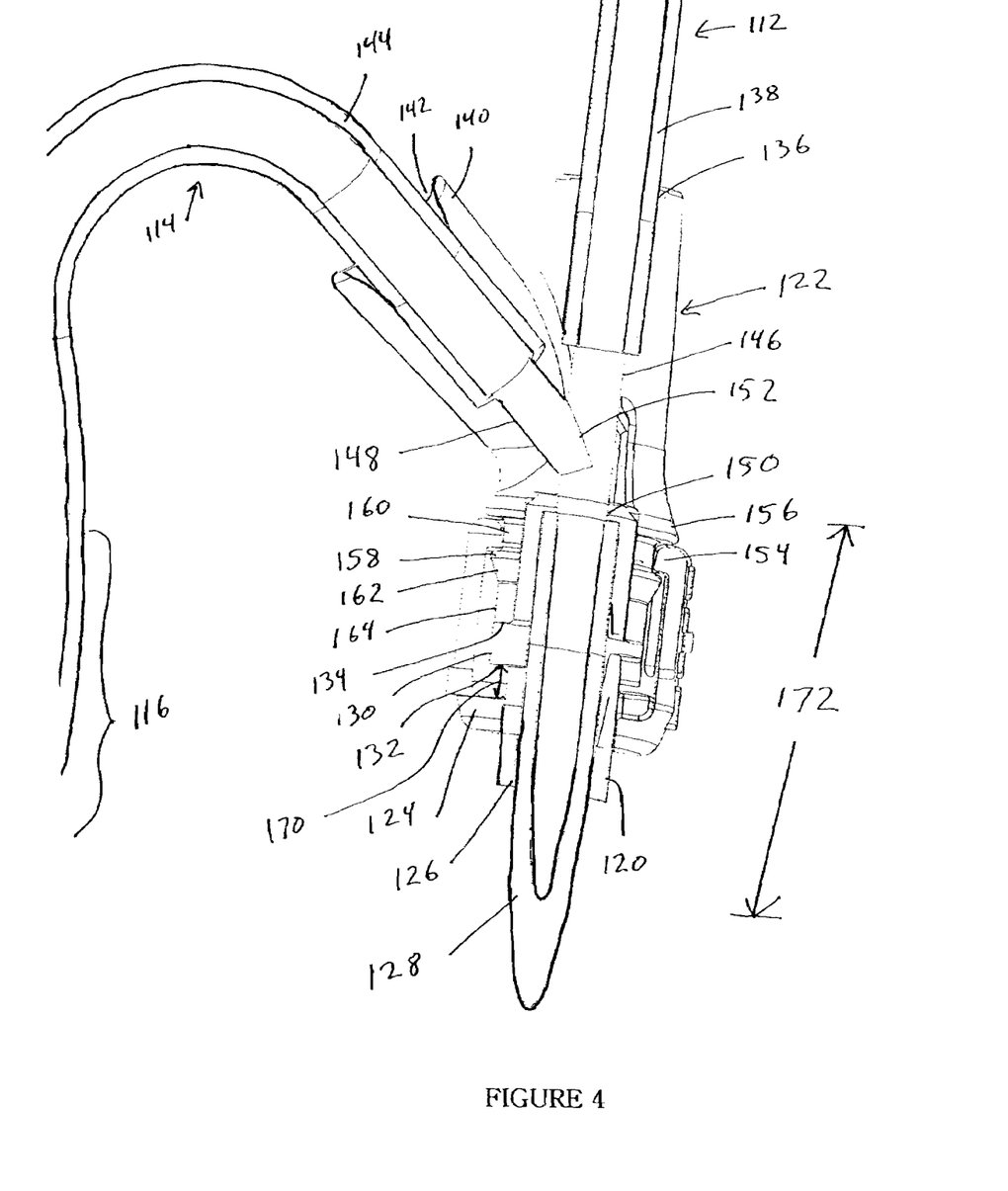
FIG. 4 is a cutaway side view.

The dimension 172 indicates the position along the device for the patient's teeth and lips. As will be apparent, the center of gravity of the overall device, exclusive of tubes 138 and 144, will be at least proximate to, if not equivalent with or within, the level of the patient's lips and teeth, thereby further advantageously resisting extubation. As will also be readily apparent to those of skill in the art, the length of ventilator tube 144 and straight port tube 138 allows for relatively remote placement of heavy equipment associated with their use and thereby reduce the possibility of inadvertent extubation. Moreover, equipment associated with each of the two tubes may be separated, thereby even further reducing the chances of inadvertent extubation.

Figure 5:
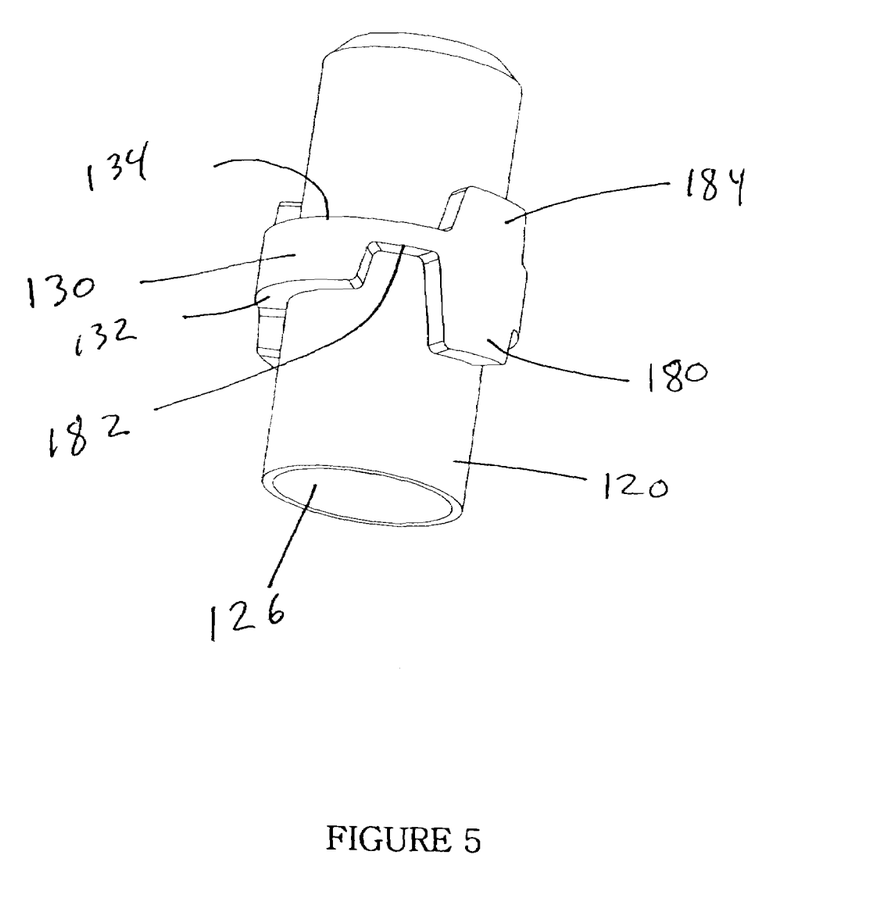
FIG. 5 is a disassembled view.
Figure 6:
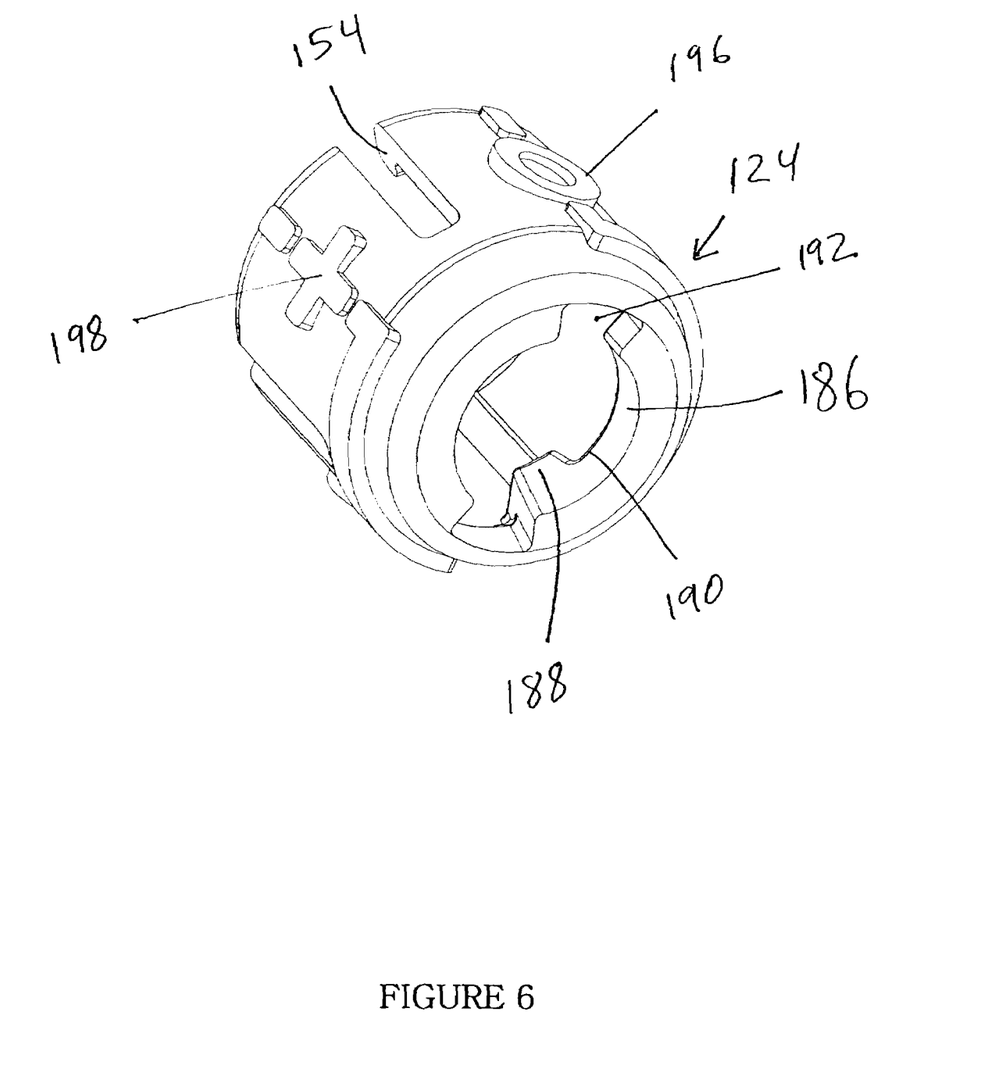
FIG. 6 is a disassembled view.

The locking features of the present invention are best illustrated with reference to FIGS. 5, 6 and 7, showing isometric views of the cuff 120, locking ring 124 and manifold 122, respectively, as separate parts. As seen in FIG. 5, the annular ring 130 around the cuff 120 includes a first release boss or tooth 180, integrally formed with annular ring 130 in the depicted embodiment, and oriented in an axial direction towards the patient. It is immediately adjacent to a release notch or detent 182 on the same step 132 as the first release tooth 180. These are dimensioned to correspond to and interact with features on the annular ring 186 of the locking ring 124, specifically, second release the tooth or boss 188 on annular ring 186. Second release tooth 188 is oriented axially away from the patient, and is dimensioned to correspond to the release notch 182 in the annular ring 130 of cuff 120. When the device is locked, second release tooth 188 and release notch 182 and first release tooth 180 and an upper surface 190 of annular ring 186 are engaged in close cooperation.

The lock tooth 184, projects from step surface 134 on annular ring 130 of cuff 120 in an axial direction away from the patient. Lock tooth 184 corresponds with lock notch 194 in extension 164 of manifold 122. When engaged, the engagement of lock tooth 184 with lock notch 194 prevents rotation of the manifold relative to the cuff 120.

The device remains in the intubated patient in a locked and safe position. In this position, this locking tooth 184 is engaged with the lock notch 194 and the release notch 180 is not aligned with gap 192 in the annular ring 186 of lock ring 124. Instead, the release tooth 180 proximal surface abuts an inner surface 190 of annular ring 186 of locking ring 124, thus restraining the locking ring 124 and cuff 120 from axial translation.

In use, to execute rotation of the device, the locking tooth 184 must be disengaged from the lock notch 194 by axial translation. In order to allow this axial translation, the locking ring must first be rotated to align release tooth 180 with gap 192 in annular ring 186.

Then, the locking ring is translated relative to cuff 120 such that release tooth 180 advances into gap 192 and second release tooth 188 advances into notch 182. Thus, a degree of translation is allowed sufficient to disengage the lock tooth 184 from the lock notch 194. The engagement of second release tooth 188 and release notch 182 prevents the locking ring 124 from axially translating farther than is necessary.

With the cuff 120 translated relative to the manifold 122 across dimension 170 (FIG. 4), thus releasing tooth 184 from its engagement with notch 194, the manifold 122 is free to rotate relative to the cuff 120. Upon rotating the manifold and ferrule—without corresponding rotation of the cuff 120 or the endotracheal tube attached to it—the tooth 184 may be reengaged with the opposing notch 194, 180° opposite the device's original position, thus allowing the mandibular portion 116 to be approximated to the other side of the patient's mandible.

Upon completion of the 180° rotation, the locking ring 124 is translated axially away from the patient, thereby reengaging lock tooth 184 with lock notch 194. With the locking features reengaged, the locking ring 124 may thereafter be rotated again, approximately 90° in the depicted embodiment, in order to bring first release tooth 180 out of alignment with gap 192 and thereafter to reengage a first release tooth 180 with surface 190, to securely seat the device in its locked and safe position for long term intubation.

Indicators 196, 198 and 199 are placed on the exterior surface of the locking ring 124 and manifold 122, in order to assist the user with alignment for locking and rotating.

Figure 8:
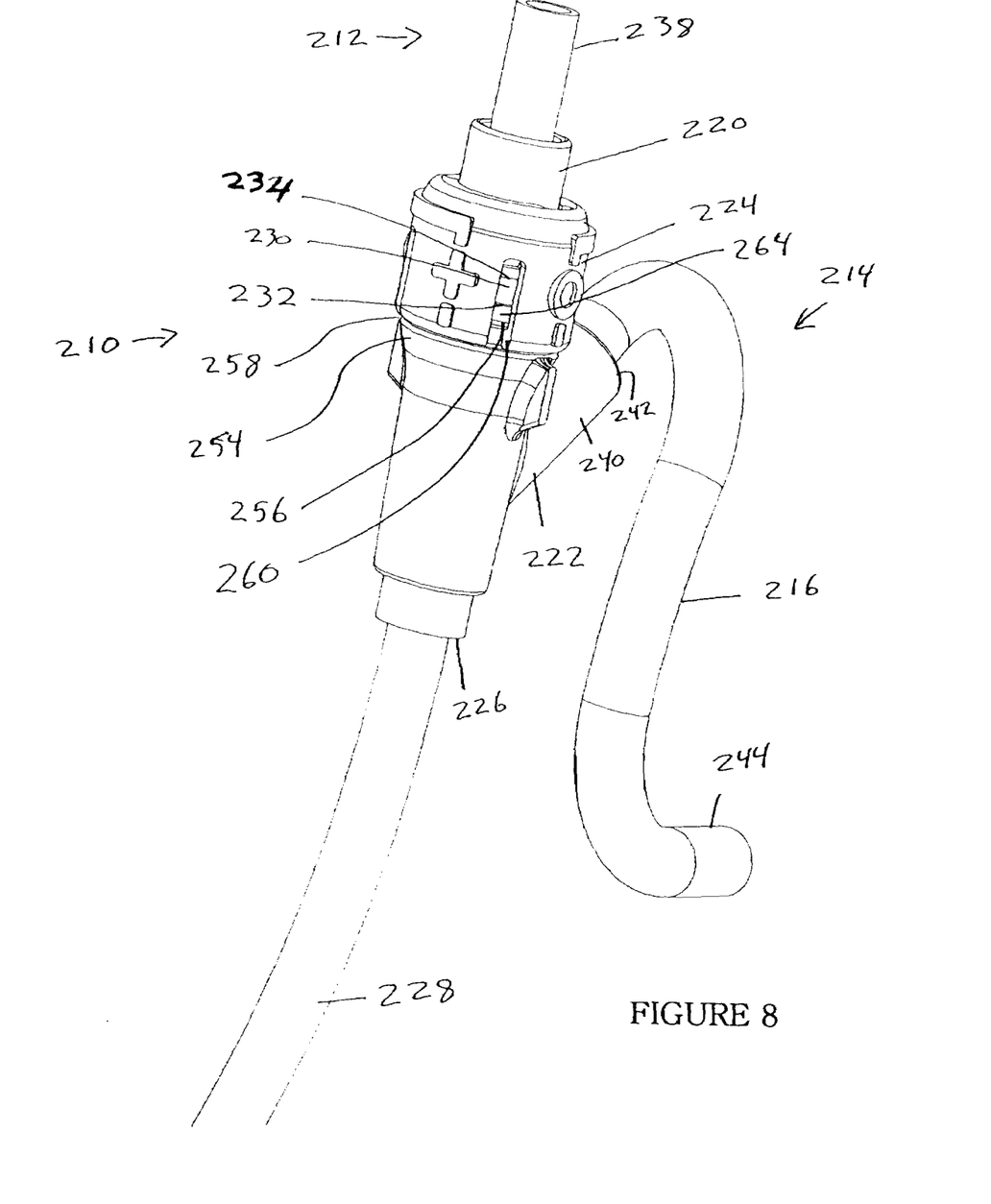
FIG. 8 is a side view of a second embodiment.

FIG. 8 depicts an isometric view of a second embodiment 210 that includes a straight port 212 and a curved port 214. Curved port 214 is shaped and dimensioned to include a mandibular portion 216 which, when the tube is in place in the patient, lies adjacent to and in contact with the patient's mandible. Thus, the mandibular portion 216 provides a second anchoring position for the endotracheal tube by such standard means as taping. The second anchoring position advantageously contributes to the prevention of inadvertent extubations. Mandibular portion 216 may be anchored to either side of the patient's mandible.

The endotracheal tube is further comprised of cuff 220, manifold 222 and locking ring 224. The cuff 220 includes a cylindrical seat 226 dimensioned to receive in close cooperation tube 228 which is the endotracheal tube portion that is installed in a patient's mouth, throat and trachea. The cuff 220 is further comprised of an annular ring 230 having integrally formed proximal and distal steps 232 and 234.

Figure 9:
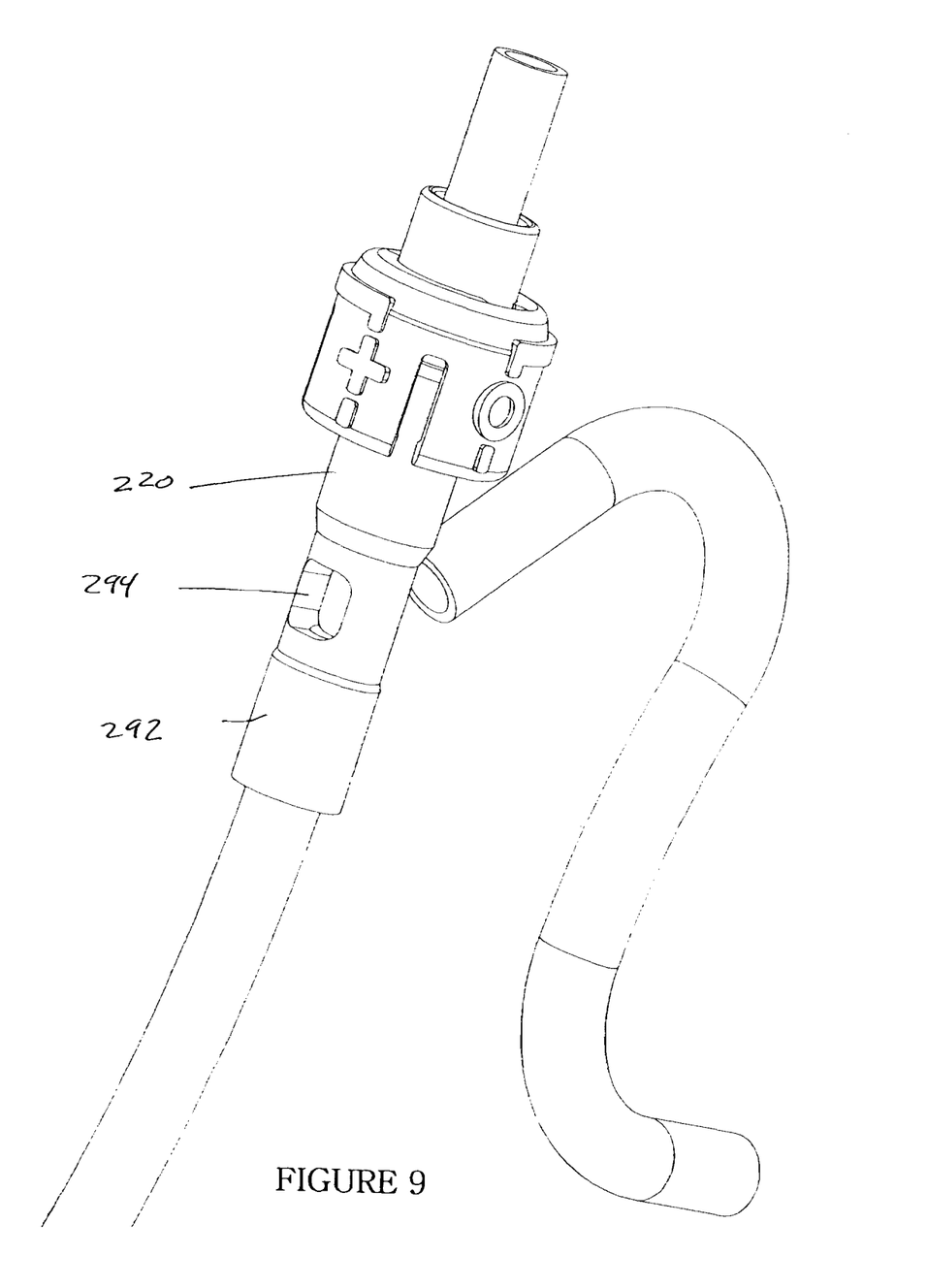
FIG. 9 is a partially disassembled view of the second embodiment.

The second embodiment varies from the first in that the locking ring is outside the split between the ports 212 and 214 relative to the patient. Accordingly, the cuff 220 varies in the second embodiment from the first embodiment in that the cuff 220 includes an extension 292 that extends through the fork and the manifold 222. As is best seen in FIG. 9, in order to create fluid communication (an airway) from the endotracheal tube 228 to the side port 214, bilaterally opposed windows 294 are formed in the extension 292 of cuff 220.

Figure 10:
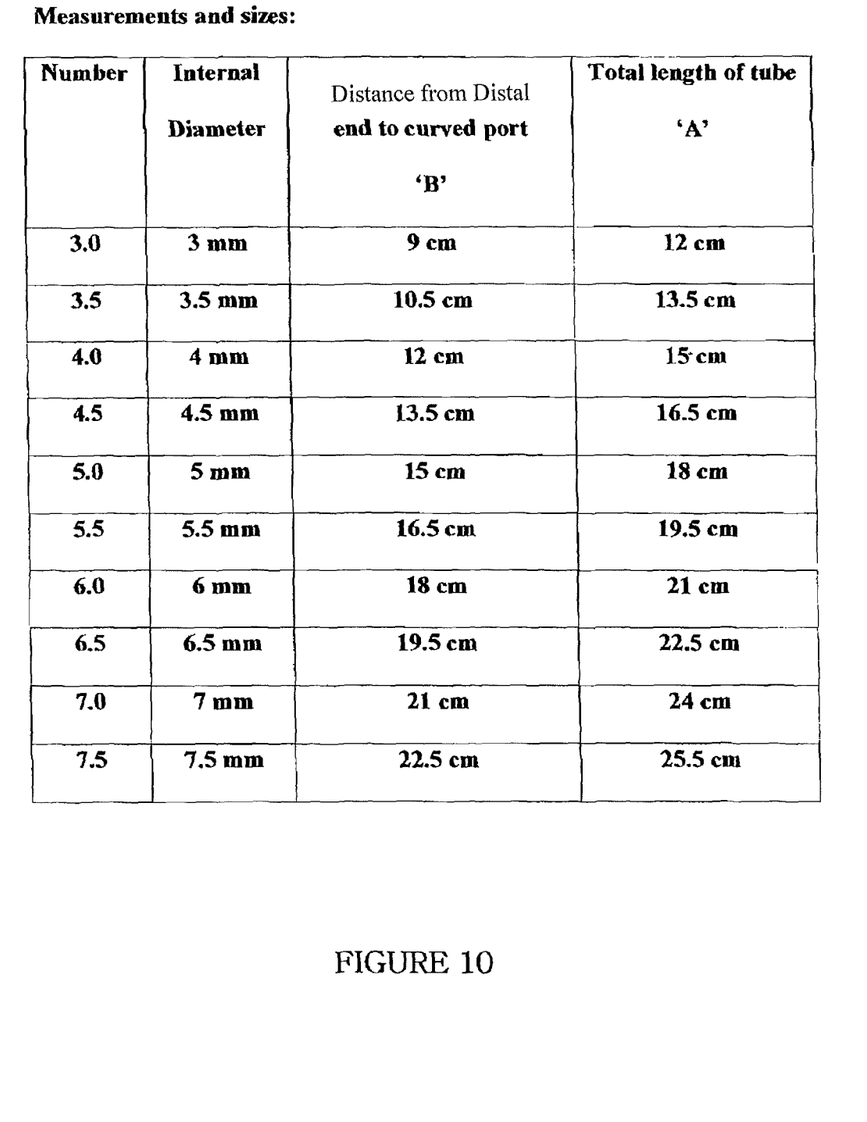
FIG. 10 is a table of dimensions.

Manifold 222 is further comprised of ferrule 240 which includes an integrally formed seat 242 dimensioned to receive in close cooperation ventilator curved port tube 244, which will typically be used for ventilation. Within manifold 222 are a straight port lumen and a ferrule lumen. As in the first embodiment, obscured in the isometric view, cuff 220 also includes an exit lumen. The internal diameter of endotracheal tube 228, cuff exit lumen, straight port internal lumen, ferrule lumen, straight port tube 238 and ferrule tube 244 are all constructed and dimensioned to avoid any flow restrictions. That is to say, the internal diameter of all these components is substantially equivalent in the depicted embodiment. This dimension may be 5 millimeters, 6 millimeters, such as are consistent with commonly used endotracheal tube components and ventilators or maybe other dimensions such as indicated in FIG. 10 within the scope of the present invention. Of note is the juncture of the ferrule lumen and straight port lumen which also is constructed and dimensioned to avoid flow restrictions.

Manifold 242 has a proximal end including a groove 254 which is defined between two annular rings 256 and 258. Groove 254 is dimensioned to receive a corresponding inward facing annular ring 260 in the lock ring 224. A leading or proximal face of inner, proximal manifold ring 258 is inclined such that the manifold 222 may be assembled with the locking ring 224 in a snap fit. The more distal or outer manifold ring 256 has a larger diameter than the inner proximal ring 258 in order to maintain locking ring 224 in its proper assembled position. Finally, the manifold's proximal section includes an annular extension 264 which after assembly abuts the distal step 234 of the annular ring 230 and cuff 220.

As is clear to those of skill in the art, the above described interaction interassembly of cuff 220, locking ring 224 and manifold 222 allows for the manifold, and accordingly ferrule 240 and ventilator tube 244 to be rotated around cuff 220 and endotracheal tube 228. Fluid communication from endotracheal tube 228 to ventilator tube 244 is through one of windows 294.

The position of ferrule 240 and ventilator 244 is advantageously limited to either of two positions. These positions correspond to the left and right side of the patient's mandible, being optimal positions for anchoring the mandibular portion 216 of the ventilator tube 244. Accordingly, the interaction of manifold extension 264 and the annular ring 230 of cuff 220 provides for locking the device at either position, and moreover for unlocking the device for rotation between the two positions. The rotation, release and locking mechanism is substantially equivalent to the locking, rotation and release mechanism described above for the first embodiment.

The dimension 272 indicates the position along the device for the patient's teeth and lips. As will be apparent, the center of gravity of the overall device, exclusive of tubes 238 and 244, will be at least proximate to, if not equivalent with or within, the level of the patient's lips and teeth, thereby further advantageously resisting extubation. As will also be readily apparent to those of skill in the art, the length of ventilator tube 244 and straight port tube 238 allows for relatively remote placement of heavy equipment associated with their use and thereby reduce the possibility of inadvertent extubation. Moreover, equipment associated with each of the two tubes may be separated, thereby even further reducing the chances of inadvertent extubation.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An endotracheal tube apparatus comprising:
   an endotracheal tube having a central passage, a proximal end and a distal end, said endotracheal tube having a lower portion extending to said distal end and said distal end arranged for insertion entirely into a patient's trachea through the patient's mouth;
   wherein when the endotracheal tube is in a fully inserted position, said proximal end is configured to extend upwardly from a patient's mouth;
   a first port at said proximal end of said endotracheal tube and in fluid communication with said central passage, said first port being oriented to extend along an axis of said proximal end when said endotracheal tube is inserted;
   wherein said proximal end of said endotracheal tube provides a first location for securing said apparatus to a patient;
   a second port adjacent said proximal end of said endotracheal tube and in fluid communication with said central passage and said first port, said second port extending at an angle to said first port; and
   said second port having a mandibular portion; said mandibular portion comprising a first portion extending in a first direction that is toward the distal end of the endotracheal tube and a second portion extending from said first portion in a second direction that is different from said first direction, said second portion being configured to attach to tubing without bending, wherein said mandibular portion is configured to be secured to a patient's mandible when said endotracheal tube is inserted; and wherein said mandibular portion provides a second location configured to secure said apparatus to said patient.

2. The endotracheal tube apparatus of claim 1 wherein a center of gravity of said apparatus is configured to be positioned proximate to the patient's lips when the endotracheal tube is inserted.

3. The endotracheal tube apparatus of claim 1 wherein said mandibular portion comprises a first portion that extends at an upward angle from said second port and then curves in a downward arc and a second portion that extends downward toward the distal end of said endotracheal tube, and wherein each of said first and second portions are configured to provide alternate points of securement to a patient's mandible.

4. An endotracheal tube apparatus comprising:

an endotracheal tube having a central passage, a proximal end and a distal end, said distal end and said endotracheal tube having lower portion with a consistent diameter through said distal end and said distal end arranged for insertion entirely into a patient's trachea through the patient's mouth;

wherein when the endotracheal tube is in a fully inserted position, said proximal end is configured to extend upwardly from a patient's mouth;

a first port in fluid communication with said central passage, said first port being oriented to extend along an axis of said proximal end when said endotracheal tube is inserted;

a second port in fluid communication with said central passage and said first port, said second port being configured to be positioned to extend at an angle to said first port when said endotracheal tube is inserted;

said second port having a curved extension portion configured for contacting, without bending, the patient's mandible when installed and attaching to tubing; and a rotation mechanism, said rotation mechanism being configured to change a position of said second port relative to said first port.

5. The apparatus of claim 4 wherein said rotation mechanism is configurable to reposition said second port from a first position to a second position, said second position being oriented opposite to said first position.

6. The apparatus of claim 4 further comprising a lock, said lock fixing a position of said second port relative to said first port and said lock being selectively releasable to allow rotation of said second port to a different position relative to said first port.

7. The apparatus of claim 4 wherein said first port rotates with said second port during rotation.

8. The endotracheal tube apparatus of claim 4 wherein said extension comprises a first portion that extends at an upward angle from said second port and then curves in a downward arc and a second portion that extends downward toward the distal end of said endotracheal tube, and wherein each of said first and second portions are configured to provide alternate points of securement to a patient's mandible.

9. An endotracheal tube apparatus configured to be placed in a patient's mouth with a first portion configured to be inserted into the patient's throat and a second portion configured to extend from the patient's mouth when said first portion is inserted, said endotracheal tube apparatus comprising:

an endotracheal tube having a central passage, a proximal end, and a distal end, said first portion having a consistent diameter extending to said distal end and said distal end arranged for insertion entirely into a patient's trachea through the patient's mouth;

a first port, said first port having a longitudinal extent and defining a longitudinal axis;

a second port, said second port beginning at an exit along said extent of said first port;

a cuff, said cuff defining a seat, said seat having an opening oriented towards said proximal end of the endotracheal tube and said seat being dimensioned for receiving an endotracheal tube;

said second port and said first port both being in fluid communication with the central passage and with each other when the endotracheal tube is seated in said seat;

said second port extending laterally away from said longitudinal axis and said second port having a mandibular portion comprising a fixed structure having a first portion extending parallel to said longitudinal axis toward said distal portion of said endotracheal tube and a second portion extending from said first portion in a second direction that is different from said first direction, wherein said mandibular portion is configured to receive a tube and to be secured to a patient's mandible when said endotracheal tube apparatus is inserted.

10. The endotracheal tube apparatus of claim 9 wherein said second port is rigid.

11. The endotracheal tube apparatus of claim 9, wherein said endotracheal tube is configured for securing to a patient at at least two locations, one of said locations being adjacent to an underside or side of a patient's mandible.

12. The endotracheal tube apparatus of claim 9 wherein a center of gravity of said apparatus is proximate to said exit of said second port.

13. The apparatus of claim 9 wherein said apparatus is configured for coordinated movement with a patient's head, when the patient's head moves.

14. The apparatus of claim 9 wherein an angle between said first port and said second port is between 1 and 135 degrees.

15. The endotracheal tube apparatus of claim 9 wherein said second port can rotate around said first port.

16. The apparatus of claim 15 wherein said first port rotates with said second port during rotation.

17. The apparatus of claim 9 further comprising a rotation mechanism, said rotation mechanism being configurable to reposition said second port from a first position to a second position, said second position being oriented opposite to said first position.

18. The apparatus of claim 17 further comprising a lock, said lock fixing a position of said second port relative to said first port and said lock being selectively releasable to allow rotation of said second port to a different position relative to said first port.

19. The endotracheal tube apparatus of claim 18 wherein said lock is comprised of a locking ring.

20. The endotracheal tube apparatus of claim 19 wherein said locking ring is located outside said exit of said second port.

21. The endotracheal tube apparatus of claim 9 further comprising a manifold, said manifold having a ferrule, said ferrule comprising said exit from said first port to said second port.

22. The endotracheal tube apparatus of claim 21 wherein said manifold and said ferrule are rotatable around said cuff, without rotating said cuff or the endotracheal tube.

23. The endotracheal tube of claim 9 wherein said second port is located at about a position that is 30 times the tube's diameter from the proximal, inner distal end of the endotracheal tube.

* * * * *